US011002809B2

(12) United States Patent
Rapoport

(10) Patent No.: US 11,002,809 B2
(45) Date of Patent: May 11, 2021

(54) PROTECTIVE AND IMMOBILIZING SLEEVES WITH SENSORS, AND METHODS FOR REDUCING THE EFFECT OF OBJECT MOVEMENT DURING MRI SCANNING

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 961 days.

(21) Appl. No.: 15/310,768

(22) PCT Filed: May 13, 2015

(86) PCT No.: PCT/IL2015/050504
§ 371 (c)(1),
(2) Date: Nov. 13, 2016

(87) PCT Pub. No.: WO2015/173817
PCT Pub. Date: Nov. 19, 2015

(65) Prior Publication Data
US 2017/0082703 A1 Mar. 23, 2017

Related U.S. Application Data

(60) Provisional application No. 61/992,312, filed on May 13, 2014, provisional application No. 62/015,539, filed on Jun. 23, 2014.

(51) Int. Cl.
*G01R 33/28* (2006.01)
*G01R 33/422* (2006.01)
(Continued)

(52) U.S. Cl.
CPC ............ *G01R 33/288* (2013.01); *A61B 5/055* (2013.01); *G01R 33/28* (2013.01);
(Continued)

(58) Field of Classification Search
None
See application file for complete search history.

(56) References Cited

U.S. PATENT DOCUMENTS 5,159,929 A 11/1992 Moriss et al.
5,166,875 A 11/1992 Machida
(Continued)

FOREIGN PATENT DOCUMENTS

CA 2826694 4/2014
EP 0637387 10/1997
(Continued)

OTHER PUBLICATIONS

International Search Report of PCT Application No. PCT/IL2015/050504, dated Dec. 18, 2015.
(Continued)

*Primary Examiner* — Katherine L Fernandez
(74) *Attorney, Agent, or Firm* — Loeb & Loeb LLP

(57) ABSTRACT

A protective sleeve reduces electromagnetic energy propagation from the magnet bore of a magnetic resonance imaging device (MRD) to the surrounding environment and prevents electromagnetic energy in the surrounding environment from contaminating an MRI reading. The protective sleeve comprises a distal portion configured for insertion within the bore and a proximal portion attachable to the MRD aperture. The sleeve is configured for inserting a body part for insertion within the MRD's open magnet, with the imaged portion of the body part protruding from the distal end of sleeve into the MRD's volume of interest. The sleeve comprises, or is connected to, one or more sensors configured to detect movement, acceleration or dislocation of at least one portion or segment of the body part to be scanned.

19 Claims, 9 Drawing Sheets

(51) Int. Cl.
  *G01R 33/565* (2006.01)
  *A61B 5/055* (2006.01)
  *G01R 33/34* (2006.01)
(52) U.S. Cl.
  CPC ....... *G01R 33/3403* (2013.01); *G01R 33/422* (2013.01); *G01R 33/56509* (2013.01)

(56) References Cited

U.S. PATENT DOCUMENTS

| | | |
|---|---|---|
| 5,304,932 A | 4/1994 | Carlson |
| 5,332,968 A | 7/1994 | Brown |
| 5,400,787 A | 3/1995 | Marandos |
| 5,427,101 A | 6/1995 | Sachs et al. |
| 5,602,891 A | 2/1997 | Pearlman |
| 5,713,364 A | 2/1998 | DeBaryshe et al. |
| 5,813,987 A | 9/1998 | Modell et al. |
| 5,986,531 A * | 11/1999 | Carrozzi ............. G01R 33/422 324/318 |
| 6,138,302 A | 10/2000 | Sashin et al. |
| 6,275,722 B1 | 8/2001 | Martin et al. |
| 6,426,623 B1 | 7/2002 | Bernstein |
| 6,591,128 B1 | 7/2003 | Wu et al. |
| 6,683,456 B1 | 1/2004 | Kinanen |
| 6,804,384 B2 | 10/2004 | Lowen |
| 6,961,606 B2 | 11/2005 | DeSilets et al. |
| 7,039,266 B1 | 5/2006 | Doty |
| 7,145,336 B2 | 12/2006 | Brown |
| 7,266,406 B2 | 9/2007 | Kroeckel |
| 7,340,125 B1 * | 3/2008 | Doty ............... G02B 6/3574 385/140 |
| 7,400,147 B2 | 7/2008 | Rapoport |
| 7,772,503 B2 | 8/2010 | Gianneschi |
| 7,801,613 B2 | 9/2010 | Li et al. |
| 8,290,228 B2 | 10/2012 | Cohen et al. |
| 8,807,084 B2 | 8/2014 | Rapoport et al. |
| 8,851,018 B2 | 10/2014 | Rapoport et al. |
| 8,896,310 B2 | 11/2014 | Rapoport |
| 9,557,397 B2 | 1/2017 | Rapoport |
| 9,568,571 B2 | 2/2017 | Rapoport |
| 9,655,542 B2 | 5/2017 | Rapoport |
| 9,720,065 B2 | 8/2017 | Rapoport |
| 9,864,029 B2 | 1/2018 | Rapoport |
| 9,864,030 B2 | 1/2018 | Rapoport |
| 9,974,705 B2 | 5/2018 | Rapoport |
| 10,031,196 B2 | 7/2018 | Rabinovitz |
| 10,078,122 B2 | 9/2018 | Rapoport |
| 10,094,896 B2 | 10/2018 | Rapoport |
| 10,132,887 B2 | 11/2018 | Rapoport |
| 10,292,617 B2 | 5/2019 | Rapoport |
| 2002/0077539 A1 * | 6/2002 | Schmit ............... A61B 6/0442 600/410 |
| 2002/0093336 A1 | 7/2002 | Bernstein |
| 2003/0076925 A1 | 4/2003 | DeSilets et al. |
| 2003/0193332 A1 | 10/2003 | Shah |
| 2003/0193515 A1 | 10/2003 | Hill et al. |
| 2004/0171927 A1 | 9/2004 | Lowen et al. |
| 2005/0033123 A1 | 2/2005 | Gardner et al. |
| 2005/0054910 A1 | 3/2005 | Tremblay et al. |
| 2005/0110489 A1 | 5/2005 | Miyoshi |
| 2005/0148845 A1 | 7/2005 | Dean et al. |
| 2005/0240098 A1 | 10/2005 | Zhong et al. |
| 2006/0052685 A1 | 3/2006 | Cho et al. |
| 2006/0079754 A1 | 4/2006 | Welch et al. |
| 2006/0257027 A1 | 11/2006 | Hero et al. |
| 2006/0258941 A1 | 11/2006 | Cable et al. |
| 2007/0010896 A1 | 1/2007 | Gray et al. |
| 2007/0249929 A1 | 10/2007 | Jeong et al. |
| 2008/0019919 A1 | 1/2008 | Rustum et al. |
| 2008/0023010 A1 * | 1/2008 | Inman ............... G01R 33/422 128/846 |
| 2008/0060843 A1 | 3/2008 | Ginanneschi |
| 2008/0087833 A1 | 4/2008 | McCroskey et al. |
| 2008/0144910 A1 | 6/2008 | Weissenborn |
| 2009/0018433 A1 | 1/2009 | Kassai et al. |
| 2009/0092305 A1 | 4/2009 | Ditt |
| 2010/0016936 A1 | 1/2010 | Stevenson et al. |
| 2010/0222671 A1 | 9/2010 | Cohen et al. |
| 2010/0228076 A1 | 9/2010 | Blank et al. |
| 2010/0290693 A1 | 11/2010 | Cohen et al. |
| 2011/0112395 A1 | 5/2011 | Ichikawa et al. |
| 2011/0142316 A1 | 6/2011 | Wang et al. |
| 2011/0162652 A1 | 7/2011 | Rapoport |
| 2011/0186049 A1 | 8/2011 | Rapoport |
| 2011/0201916 A1 | 8/2011 | Duyn et al. |
| 2011/0221439 A1 | 9/2011 | Posse |
| 2011/0230755 A1 | 9/2011 | MacFarlane |
| 2011/0234347 A1 | 9/2011 | Rapoport |
| 2011/0270362 A1 * | 11/2011 | Goedeke ............... A61N 1/05 607/63 |
| 2011/0282181 A1 | 11/2011 | Wang et al. |
| 2011/0304333 A1 | 12/2011 | Rapoport |
| 2012/0043963 A1 | 2/2012 | Rapoport |
| 2012/0065494 A1 | 3/2012 | Gertner et al. |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0119742 A1 | 5/2012 | Rapoport |
| 2012/0165654 A1 | 6/2012 | Rapoport |
| 2012/0243756 A1 | 9/2012 | Samsonov et al. |
| 2012/0265045 A1 * | 10/2012 | Stevenson ............ A61B 5/6852 600/373 |
| 2013/0079624 A1 | 3/2013 | Rapoport |
| 2013/0093866 A1 | 4/2013 | Ohlhues |
| 2013/0109956 A1 | 5/2013 | Rapoport |
| 2013/0229177 A1 | 9/2013 | Bammer et al. |
| 2013/0237803 A1 | 9/2013 | Rapoport |
| 2013/0328559 A1 | 12/2013 | Rapoport |
| 2013/0328560 A1 | 12/2013 | Rapoport |
| 2013/0328563 A1 | 12/2013 | Rapoport |
| 2013/0345546 A1 | 12/2013 | Hobeika |
| 2014/0004427 A1 | 1/2014 | Medoff et al. |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051975 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0171784 A1 | 6/2014 | Ooi |
| 2014/0219531 A1 | 8/2014 | Epstein et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0275966 A1 | 9/2014 | Schwartz |
| 2014/0300358 A1 | 10/2014 | Rapoport |
| 2014/0378821 A1 | 12/2014 | Rapoport et al. |
| 2014/0378825 A1 | 12/2014 | Rapoport et al. |
| 2015/0059157 A1 | 3/2015 | Rapoport |
| 2015/0059655 A1 | 3/2015 | Rapoport |
| 2015/0065788 A1 | 3/2015 | Rapoport |
| 2015/0066413 A1 | 3/2015 | Bhagat et al. |
| 2015/0073204 A1 | 3/2015 | Rapoport |
| 2015/0077105 A1 | 3/2015 | Rapoport et al. |
| 2015/0084630 A1 | 3/2015 | Rapoport |
| 2015/0087051 A1 | 3/2015 | Rapoport |
| 2015/0123657 A1 | 5/2015 | Rapoport |
| 2015/0126804 A1 | 5/2015 | Rapoport |
| 2015/0137812 A1 | 5/2015 | Rapoport |
| 2015/0141799 A1 | 5/2015 | Rapoport et al. |
| 2015/0150511 A1 * | 6/2015 | Van Helvoort ........ A61B 5/721 600/421 |
| 2015/0160311 A1 | 6/2015 | Rapoport et al. |
| 2015/0208994 A1 | 7/2015 | Rapoport |
| 2015/0231012 A1 | 8/2015 | Rapoport |
| 2015/0253397 A1 | 9/2015 | Rapoport |
| 2015/0253400 A1 | 9/2015 | Rapoport |

(56) References Cited

U.S. PATENT DOCUMENTS

| | | |
|---|---|---|
| 2015/0253401 A1 | 9/2015 | Rapoport |
| 2015/0257675 A1 | 9/2015 | Bottomley et al. |
| 2015/0265219 A1 | 9/2015 | Feiweier et al. |
| 2016/0077171 A1 | 3/2016 | Rabinovitz et al. |
| 2016/0077176 A1 | 3/2016 | Rabinovitz et al. |
| 2016/0077180 A1 | 3/2016 | Beck |

FOREIGN PATENT DOCUMENTS

| | | |
|---|---|---|
| EP | 0825450 | 2/1998 |
| EP | 1400202 | 3/2004 |
| EP | 1898206 | 3/2008 |
| JP | 2005152114 | 6/2005 |
| JP | 2007532259 | 11/2007 |
| JP | 2011527222 | 10/2011 |
| WO | WO 2005101045 | 10/2005 |
| WO | WO 2007136745 | 11/2007 |
| WO | WO 2008028904 | 3/2008 |
| WO | WO 2010004427 | 1/2010 |
| WO | WO 2010041206 | 4/2010 |
| WO | 2011127942 | 10/2011 |
| WO | WO 2013/190451 | 12/2013 |
| WO | WO 2013190451 | 12/2013 |

OTHER PUBLICATIONS

Zaitsev, Maxim, et al. "Magnetic resonance imaging of freely moving objects: prospective real-time motion correction using an external optical motion tracking system." *Neuroimage* 31.3 (2006): pp. 1038-1050.

Ranieri, Shawn Michael. "Development of Simulator Training to Reduce Head Motion Artifact in fMRI" Diss. University of Toronto. 2011. pp. 1-60.

Zoroofi, Reza Aghaeizadeh, et al. "MRI artifact cancellation due to rigid motion in the imaging plane." *IEEE transactions on medical imaging* 15.6 (1996): pp. 768-784.

Andrews-Shigaki, B. C., Armstrong, B. S., Zaitsev, M., & Ernst, T. (2011). Prospective motion correction for magnetic resonance spectroscopy using single camera retro-grate reflector optical tracking. Journal of Magnetic Resonance Imaging, 33(2), 498-504.

Extended European Search Report issued by the European Patent Office dated Jun. 2, 2014 in corresponding European Application No. 13187323.4-1560, 11 pages.

Frost, R., Hess, A. T., Okell, T. W., Chappell, M.A., Tisdall, M. D., van der Kouwe, A. J., & Jezzard, P. (2016). Prospective motion correction and selective reacquisition using volumetric navigators for vessel-encoded arterial spin labeling dynamic angiography. Magnetic resonance in medicine. 11 pages.

Singh, A., Zahneisen, B., Keating, B., Herbst, M., Chang, L., Zaitsev, M., & Ernst, T. (2015). Optical tracking with two markers for robust prospective motion correction for brain imaging. Magnetic Resonance Materials in Physics, Biology and Medicine, 28(6), 523-534.

Speck, O., Hennig, J., & Zaitsev, M. (2006). Prospective real-time slice-by-slice motion correction for fMRI in freely moving subjects. Magnetic Resonance Materials in Physics, Biology and Medicine, 19(2), 55-61.

White, N., Roddey, C., Shankaranarayanan, A., Han, E., Rettmann, D., Santos, J., & Dale, A. (2010). PROMO: Real-time prospective motion correction in MRI using image-based tracking. Magnetic Resonance in Medicine, 63(1), 91-105.

Zoroofi, et al., "MRI artifact cancellation due to rigid motion in the imaging plane", Medical Imagining, IEEE Transactions on Medical Imaging, Dec. 1996, pp. 768-784, vol. 15, Issue 6, Osaka University, Japan.

Aksoy et al., Real-time optical motion correction for diffusion tensor imaging, Magnetic Resonance in Medicine, 2011, 66:366-378.

Alhamud, et al., volumetric navigators for real time motion correction in diffusion tensor imaging, Magn Reson Med. 2012, 68(4):1097-1108.

Ali et al.,The ischemic stroke patient who worsens: new assessment and management approaches, Nev Neurol Dis. 2007; 4(2):85-91.

Barral et al., Real-time motion corrrection for high resolution larynx imaging, Magn Reson Med. 2011, 44(1):174-179.

Brown, et al., Prospective motion correction of high-resolution magnetic resonance imaging data in children, NeuroImage, 2010, 53:139-145.

Caprihan et al., Flow measurement by NMR, Physics reports, 1990, 198, No. 4, 195-235.

The Cochrane Library, Organised inpatient (stroke unit) care for stroke, Stroke Unit Trialists Collaboration, Cochrane Database of Systemic Reviews, Sep. 11, 2013, Issue 9, John Wiley & Sons Ltd. USA.

Forman et al., Self-encoded marker for optical prospective head motion correction in MRI, Medical Image Analysis, 2011, 15:708-719.

Glunde et al., Will magnetic responnance imagng (MRI)-based contrast agents for molecular receptor imaging make their way into the clinic?, J Cell Mol. Med. 2008, 12(1):187-188.

Green E et al., Head movement in normal subjects during simulated PET brain imaging with and without head restraint, J Nucl Med 1994, 35:1538-1546.

Jolliffe, I.T., Principal component Anlaysis, Second Edition, Springer Series in Statistics, John Wiley & Sons, Ltd. 2002.

Kidwell et al, Establishment of primary stroke centers, Neurology 2003, 60:1452-1456.

Kumar, Y. Kiran, Comparison of fusion techniques applied to preclinical images: Fast discrete curvelet tansform using wrapping technique & wavelet transform, Journal of Theoretical and Applied Information Technology, 2009, 5.6, 668-673.

Lin et al.,Optically tunable nanoparticle contrast agents for early cancer detection: model-based analysis of gold nanoshells, Journal of Biomedical Optics 10(6), Nov./Dec. 2005, 1-10.

Ooi et al., Prospective real-time correction for arbitrary head motion using active markers, Magn Reson Med , 2009, 62:943-954.

Pipe, James G., Motion correction with propeller MRI: application to head motion and free-breathing cardiac imaging, Magn Reson Med, 1999, 42:963-969.

Qin et al., Prospective head-movement correction for high-resolution MRI using an in-bore optical tracking system, Magn Reson Med. 2009, 62:924-934.

Rajajee et al., Early MRI and outcomes of untreated patients with mild or improving ischemic stroke, Neurology 2006, 67:980-984.

Sachs et al., Real-time motion detection in spiral MRI using navigators, MRM 1994, 32:639-645.

Stroke Assessment Scales, retrieved from «http://www.strokecenter.org/professionals/stroke-diagnosis/stroke-assessment-scales/» on Apr. 29, 2015.

Zaitsev et al., Magnetic resonance imaging of freely moving objects: prospective real-time motion correction using an external optical motion tracking system, NeuroImag, 2006, 31:1038-1050.

\* cited by examiner

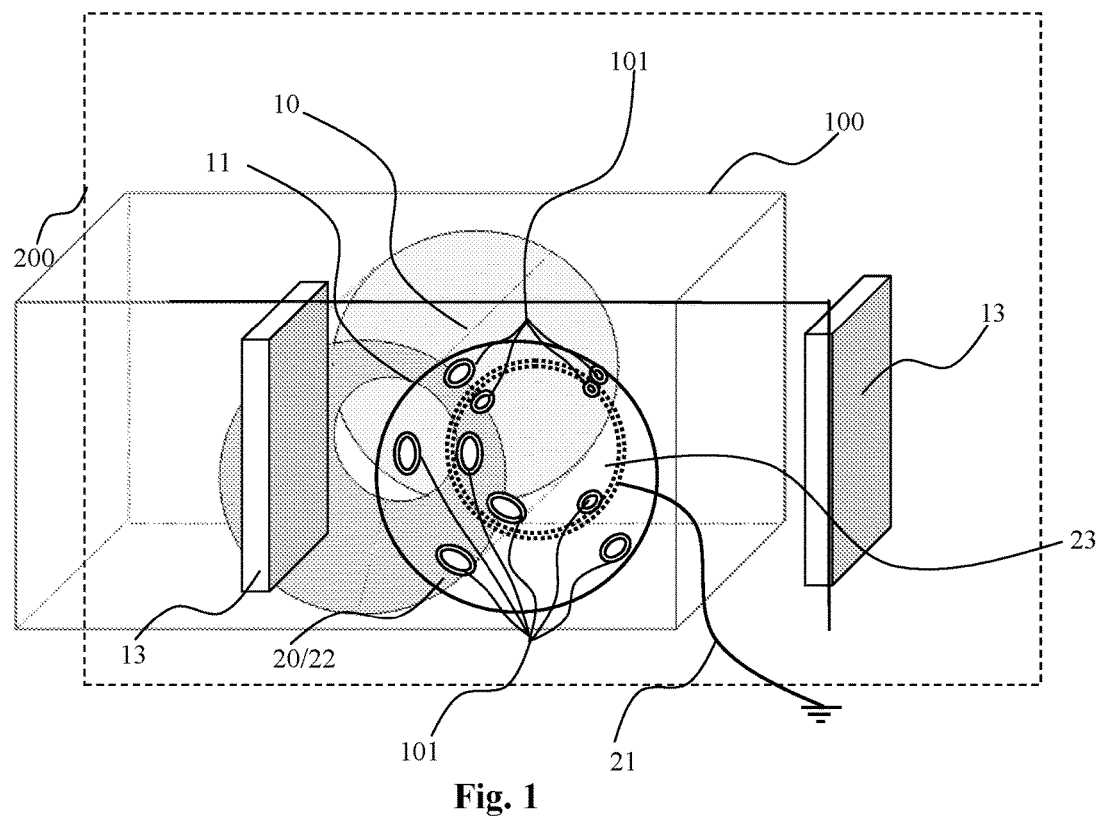
Fig. 1
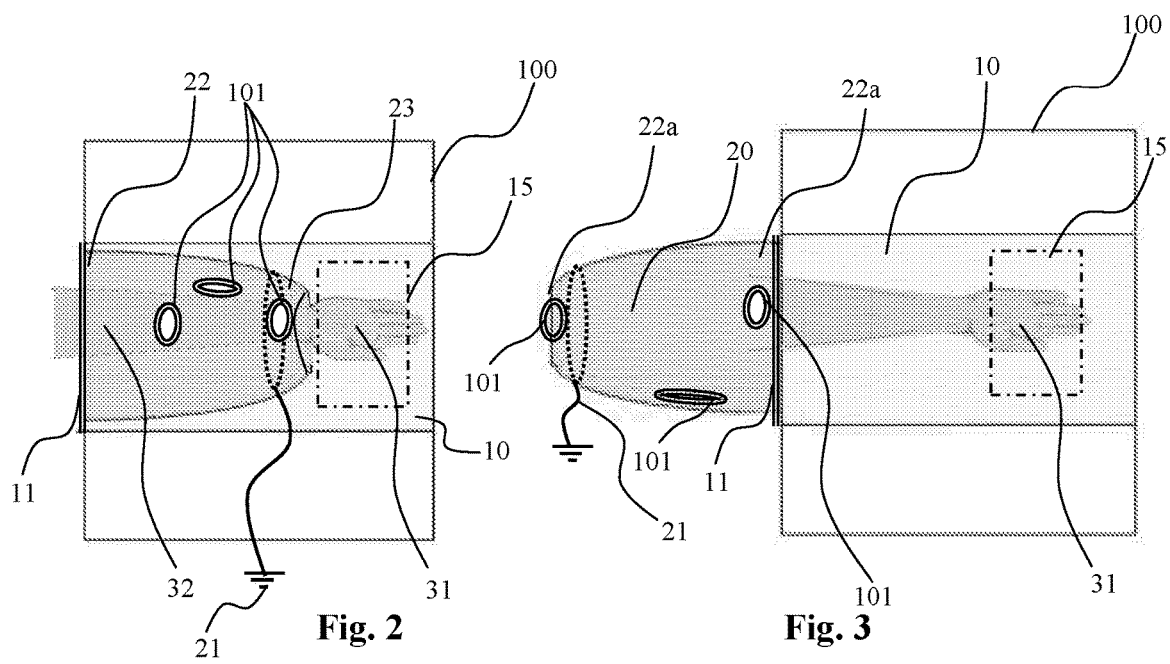
Fig. 2                    Fig. 3

Fringe field 5 Gauss line. The external line is the 5 G line.

PROTECTIVE AND IMMOBILIZING SLEEVES WITH SENSORS, AND METHODS FOR REDUCING THE EFFECT OF OBJECT MOVEMENT DURING MRI SCANNING

CROSS-REFERENCE TO RELATED APPLICATIONS

This application is a National Phase Application of PCT International Application No. PCT/IL2015/050504, International Filing Date May 13, 2015, entitled: "PROTECTIVE AND IMMOBILIZING SLEEVES WITH SENSORS, AND METHODS FOR REDUCING THE EFFECT OF OBJECT MOVEMENT DURING MRI SCANNING", published on Nov. 19, 2015 as International Patent Application Publication No. WO 2015/173817, claiming the benefit of U.S. Provisional Patent Applications No. 61/992,312, filed May 13, 2014, and Application No. 62/015,539, filed Jun. 23, 2014, all of which are hereby incorporated by reference in their entireties.

FIELD OF THE INVENTION

The present invention pertains to means, such as a protective sleeve with one or more movement sensors, and methods for reducing the effects of object movements within aforesaid protective sleeve during an MRI scan.

BACKGROUND OF THE INVENTION

This invention relates to the field of magnetic resonance imaging (MRI), where radiofrequency (RF) magnetic fields are used to interrogate a region of interest. It is particularly directed towards the shielding of RF effects which occur from inside and outside of the MRI system.

One of the components in MRI systems is an RF coil, which is part of a typical MRI data gathering sequence. MRI RF signals of suitable frequencies are transmitted into the imaging volume and NMR responsive RF signals are then received from the imaging volume via one or more RF coils or antennae. Information encoded within the frequency and phase parameters of the received RF signals is then processed to form visual images representing the distribution of NMR nuclei within a cross-section or volume of the patient within the volume of interest (VOI) of the MRI system.

In MRI devices (MRDs) which are meant for imaging body extremities, only the portion to be examined in the MRI is located within the bore of the MRI system, whereas the rest of the body remains outside of the MRI. In such cases, RF signals from the volume outside the MRI may be collected through the conductive body and the extremity to be examined. The volume outside the MRI has dielectric properties and may serve as a transceiver of RF signals, thus causing noise in signal collection during an MRI examination.

Additionally, RF fields within the MRI can induce an electrical current in the body which is transformed into energy in the form of heat. Heating of tissues is due to resistance in the tissues is called "ohmic heating". Specific Absorption Rate (SAR) is key variable in determining patient heating potential in an MR scanner is the RF power absorbed by the body per unit mass, generally measured in the unit of W/kg. If the SAR exceeds the thermal regulation capacity the patient's body temperature will rise.

U.S. Pat. No. 5,304,932 is directed towards shielding an MRI RF coil from extraneous noise sources using an extremely thin conductive shield interposed between the RF coil and the static magnetic structure of an MRI system. To control eddy currents induced in such conductor by the changing magnetic flux of MRI gradient coils, the RF shield conductor thickness is less than three skin depths at the MRI RF operating frequencies of the RF coil. Preferably, the RF shield conductor thickness is on the order of only one skin depth or less U.S. Pat. No. 7,801,613 is directed towards housing of implantable medical devices in a titanium alloy that provides improved electrical performance, mechanical strength, and reduced MRI heating.

There thus remains a long felt need for reducing the electromagnetic energy propagation from MRI's magnet bore to the outer environment surrounding the magnet and vice versa, for a protecting means providing effective Faraday shielding used as a barrier between the internal and external RF fields, and for reducing SAR of a non-examined portion of a body extremity in the vicinity of an MRD.

Subject motion and associated artifacts limit the applicability of magnetic resonance imaging (MRI) and the achievable quality of the images acquired, See Zaitsev et al., Magnetic resonance imaging of freely moving objects: prospective real-time motion correction using an external optical motion tracking system, NeuroImage 31(3), 1038-1050 (2006). Post-processing techniques have been developed to suppress MRI artifact arising from object planar rigid motion, See for example Zoroofi et al., IEEE Transaction on Medical Imaging, 15(6), 768-784 (1996). Moreover, a few patents, such as U.S. Pat. No. 5,602,891, disclose computerized tomography (CT) scanners and functional MRI (fMRI) imaging apparatus with means for compensation object motion.

As presented by Ranieri (2011), during fMRI acquisition, light restraints (i.e. foam wedges, vacuum pillows, straps, etc.) are used to help limit head motion. These restraints are most effective in restricting motion in the medial-lateral direction, and less effective for motion in orthogonal directions. With the desire to keep patient discomfort and stress at a minimum, head restraint is only lightly used and is not an extremely effective technique for preventing motion in fMRI, See https://tspace.library.utoronto.ca/bitstream/1807/29603/6/Ranieri_Shawn_M—201106_MHSc_thesis.pdf.

Hence, there remains a long-felt and unmet need for MRI devices configured for avoiding motion artifacts and specialized in producing an image sequence with reduced object-movement effects and artifacts, especially MRI systems adapted to image uncontrollably movable objects, such as neonates, premature babies and laboratory animals; and especially in those special cases were restraint is to be avoided.

SUMMARY OF THE INVENTION

It is thus one object of the present invention to disclose an electrically earthed protective sleeve for reducing (a) the electromagnetic energy propagation from the magnet bore of a magnetic resonance imaging device (MRD) to the surrounding environment, and (b) external electromagnetic energy from contaminating an MRI reading ; the protective sleeve comprises (a) a distal portion configured for insertion within the bore and (b) a proximal portion attachable to the MRD aperture; the length and diameter of the sleeve are configured to accept a non-imaged portion of a body part for insertion within the bore whilst the imaged portion protrudes from the distal end of sleeve into the MRD's volume of interest; the sleeve comprises, or is connected to, one or more sensors, at least one sensor array or a combination thereof, at least one of the sensors is configured to detect, directly or indirectly, movement, acceleration or dislocation of at least one portion or segment of a body part to be scanned or being scanned; at least one sensor is located peripherally to a portion of the body to be, or currently being, scanned.

It is another object of the present invention to disclose the device mentioned above, the protective sleeve comprising a fabric material; an intermediate conducting layer; an outer dielectric layer or an outer conducting strip; wherein the fabric sleeve is adjusted to accommodate a body extremity, the intermediate conducting layer is placed/sewn/surrounds the fabric sleeve, the outer dielectric layer is placed/sewn or surrounds the intermediate conducting layer, and the outer conducting strip is fastened to the outer dielectric layer with at least one contact with the intermediate conducting layer and at least one contact to an external earthing system.

It is another object of the present invention to disclose the device mentioned above, the protective sleeve effectively eliminating tissue heating due to RF magnetic fields during MR scanning, and limits temperature rises in excess of 1° C. and localized heating to 38° C. in the head, 39° C. in the trunk, and 40° C. in the extremities.

It is another object of the present invention to disclose the device mentioned above, the protective sleeve effectively maintaining SAR levels below recommended limits as follows: 4 Watt/kg averaged over the whole body for any 15-minute period (1.5 Watt/kg if the patient is thermally compromised, as a function of room temperature and humidity), 3.2 Watt/kg averaged over the head for any 10-minute period, and 8 W/Kg in any 1 cc of tissue in head averaged over 5 minutes.

It is another object of the present invention to disclose the device mentioned above, the protective sleeve effectively limiting the magnetic fringe field at the entrance of the MRI suite to be equal to or less than 5 Gauss, referred to as "the 5-Gauss line."

It is another object of the present invention to disclose the device mentioned above, the protective sleeve effectively preventing temperature rises, due to RF heating during MR scanning, beyond the limit of 40° C. in the body extremity.

It is another object of the present invention to disclose the device mentioned above, the protective sleeve configured to fit one or more of the body extremities, such as a toe, finger, wrist, elbow, ankle, knee, or head, as well as body non-extremities such as the abdomen, belly, and any combination thereof.

It is another object of the present invention to disclose the device mentioned above, the protective sleeve configured to provide separation means for preventing skin-to-skin contact of body parts selected from the group comprising inner thigh-to-thigh, calf-to-calf, hand-to-hand, hand-to-body, ankle-to-ankle contact, thereby preventing the formation of conductive loops through part of the body.

It is another object of the present invention to disclose the device mentioned above, the protective sleeve configured to provide a means for preventing the placement of the body extremity against an RF transmitting coil surface.

It is another object of the present invention to disclose the device mentioned above, the protective sleeve configured to provide SAR conditions conforming to the NEMA MS-8-2006 standard for MRI Systems.

It is another object of the present invention to disclose the device mentioned above, the protective sleeve adapted to fit an orifice of a body therein.

The protective sleeve of claim 1, the protective sleeve configured for compliance with Electrical & Mechanical Safety (IEC 60601-1) General requirements for basic safety and essential performance.

It is another object of the present invention to disclose the device mentioned above, the protective sleeve configured for compliance with Electromagnetic Compatibility (IEC 60601-1-2) General requirements for basic safety and essential performance—Collateral standard: Electromagnetic compatibility—Requirements and tests.

It is another object of the present invention to disclose the device mentioned above, the protective sleeve configured for compliance with IEC 60601-2-33 Medical electrical equipment—Parts 2-33: Particular requirements for the basic safety and essential performance of magnetic resonance equipment for medical diagnostic (2007 (Second Edition)+A1:2005+A2:2007).

It is another object of the present invention to disclose the device mentioned above, the protective sleeve configured for compliance with NEMA MS 4 (2010) Acoustic Noise Measurement Procedure for Diagnosing Magnetic Resonance Imaging Devices.

It is another object of the present invention to disclose the device mentioned above, the protective sleeve configured for compliance with NEMA MS 8 (2006) Characterization of the Specific Absorption Rate (SAR) for MRI Systems.

It is another object of the present invention to disclose the device mentioned above, the protective sleeve configured for compliance with NEMA MS 10 (2006) Determination of Local Specific Absorption Rate (SAR) in Diagnostic Magnetic Resonance Imaging.

It is another object of the present invention to disclose the device mentioned above, the protective sleeve configured for compliance with NEMA MS 11 (2006) Determination of Gradient-Induced Electric Fields in Diagnostic Magnetic Resonance Imaging.

It is another object of the present invention to disclose the device mentioned above, the protective sleeve configured for compliance with IEC 60601-2-33 Medical electrical equipment—Part 2-33: Particular requirements for the basic safety and essential performance of magnetic resonance equipment for medical diagnostic (2007 (Second Edition)+A1:2005+A2:2007).

It is another object of the present invention to disclose a method for avoiding object motion artifacts during MRI imaging, comprising steps of:
 (a) providing a movement sensor in, or in connection with, an RF protective/immobilizing sleeve;
 (b) acquiring a sequence of MRI consecutive images, $CI_n$, of an object;
 (c) storing on a computer readable medium (CRM) at least one parameter p indicating spatial image orientation at which said image was taken for each $CI_n$;
 (d) analyzing the sequence of the $CI_n$ for detection of the object's movement;
 (e) tagging thereby $K_M$ images, $CI_k^M$, of at least one movement M of the object; and
 (f) determining, using the tagged images $CI_k^M$ for each of movement M, the following parameters:
  i. two of the following: the movement starting time $T_{MS}$, the movement ending time $T_{ME}$, and time length of the movement $T_M$; and
  ii. the movement spatial image orientation parameter $P_{MS}$ at the beginning of the movement;
wherein the method additionally comprises, for each the M whose $T_M$ is shorter than a predetermined time length PT, steps of acquiring a sequence of $K_M$ MRI consecutive images $NCI_k^M$, starting at the $P_{MS}$ and ending after the $NCI_k^M$, replacing the $NCI_k^M$ with the $CI_k^M$ in the sequence; repeating steps (c)-(f) until no more movements are detected whose $T_M$ is shorter than the PT; thereby producing an image sequence with reduced object-movement during MRI imaging. The method thus enhances the quality of the MRI images acquired, increases SNR, and decreases associated artifacts, It is another object of the present invention to disclose a method for reducing the effect of object movements during MRI imaging; the method comprising steps of:
  (a) providing a movement sensor in or in connection with protecting/immobilizing sleeve;
  (b) acquiring a sequence of N MRI consecutive images, $CI_n$, of an object;
  (c) storing on a computer readable medium (CRM) at least one parameter p indicating spatial image orientation at which said image was taken for each $CI_n$;
  (d) analyzing, by means of one or more non-MRD-based motion detectors, the motion of the object;
  (e) tagging $K_M$ images $CI_k^M$ of at least one movement M of the object; and
  (f) determining, using the tagged images $CI_k^M$ for each of movement M, the following parameters:
    i. two of the following: the movement starting time $T_{MS}$, the movement ending time $T_{ME}$, and time length of the movement $T_M$; and
    ii. the movement spatial image orientation parameter $P_{MS}$ at the beginning of the movement;
wherein the method additionally comprises, for each the M whose $T_M$ is shorter than a predetermined time length PT, steps of acquiring a sequence of $K_M$ MRI consecutive images $NCI_k^M$ starting at the $P_{MS}$ and ending after the $T_M$; replacing the $NCI_k^M$ with the $CI_k^M$ in the sequence; repeating steps (c)-(f) until no more movements can be detected whose $T_M$ is shorter than the PT; thereby producing an image sequence with reduced object-movement in MRI imaging.

It is another object of the present invention to disclose the method as defined in any of the above, additionally comprising a step of selecting the non-MRD-based motion detectors from a group consisting of or otherwise comprising: passive infrared sensors; detectors which sense body heat; mechanical detectors; electronic detectors; optical detectors; acoustical detectors; sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors triboelectric, seismic, and inertia-switch sensors); and any combination thereof.

It is another object of the present invention to disclose the method as defined in any of the above, wherein the method additionally comprises the step of selecting the parameter from a group consisting of: angle of image with respect to the object, spatial coordinates of the area of the image, location of MRI components and a combination thereof.

It is another object of the present invention to disclose the method as defined in any of the above, wherein the method additionally comprises the step of selecting the object from a group consisting of: adult person, person under anesthesia, infant, premature baby, animal and a combination thereof.

It is another object of the present invention to disclose the method as defined in any of the above, wherein the method additionally comprises the step of characterizing at least one of the movement M by the extent of the movement.

It is another object of the present invention to disclose the method as defined in any of the above, wherein the method additionally comprises an image processing step prior to step (c); wherein the processing step comprises performing Fourier transformation on the consecutive image to momentum space (K-space).

It is another object of the present invention to disclose the method as defined in any of the above, wherein the step of analyzing is performed on images in K-space.

It is another object of the present invention to disclose an MRI system imaging a movable object, comprising: a movement sensor in, or in connection with, an RF protective/immobilizing sleeve, an MRI device adapted to produce a sequence of N MRI consecutive images $CI_n$ of an object; each of the images is characterized by at least one parameter p indicating spatial image orientation at which the image was taken; a computer readable medium (CRM) in communication with the MRD; the CRM having instructions thereon for executing a method comprising steps of:
  (a) analyzing the sequence of the $CI_n$;
  (b) tagging $K_M$ images $CI_k^M$ of at least one movement M of the object;
  (c) determining, using the tagged images $CI_k^M$ for each of movement M, the following parameters:
    i. two of the following: the movement starting time TMS, the movement ending time TME, and time length of the movement TM; and
    ii. the movement spatial image orientation parameter $P_{MS}$ at the beginning of the movement;
wherein for each the M, whose $T_M$ is shorter than a predetermined time length PT, the instructions are additionally adapted for acquiring a sequence of $K_M$ MRI consecutive images $NCI_k^M$, starting at the $P_{MS}$ and ending after the $T_M$; replacing $NCI_k^M$ with $CI_k^M$ in the sequence; and repeating steps (a)-(c) until no more movements can be detected whose $T_M$ is shorter than PT.

It is another object of the present invention to disclose the system mentioned above, wherein the non-MRD-based motion detectors are selected from a group consisting of or otherwise comprising: passive infrared sensors; detectors which sense body heat; mechanical detector; electronic detectors; optical detectors; acoustical detectors; pressure detectors, location or dislocation sensors, sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors (triboelectric, seismic, and inertia-switch sensors); and any combination thereof.

It is another object of the present invention to disclose the system mentioned above, wherein the parameter is selected from a group consisting of: angle of image with respect to the object, spatial coordinates of the area of the image, location of MRI components, and any combination thereof.

It is another object of the present invention to disclose the system mentioned above, wherein the object is selected from a group consisting of: adult person, person under anesthesia, infant, premature baby, animal, and any combination thereof.

It is another object of the present invention to disclose the system mentioned above, wherein the at least one of the movement M is characterized by the extent of the movement.

It is another object of the present invention to disclose the system mentioned above, wherein the instructions additionally for perform a Fourier transformation on the consecutive image to momentum space (K-space) prior to the analysis.

It is another object of the present invention to disclose the system mentioned above, wherein the analysis is performed on images in K-space.

It is another object of the present invention to disclose the device mentioned above, the protective sleeve described in the figures.

It is another object of the present invention to disclose the system mentioned above, the MRI system as described in the figures.

It is another object of the present invention to disclose the device mentioned above, the protective sleeve as described in the description.

It is another object of the present invention to disclose the system mentioned above, the MRI system as described in the description.

BRIEF DESCRIPTION OF FIGURES

In order to understand the invention and to see how it may be implemented in practice, and by way of non-limiting example only, the disclosure will provide details in the subsequent description of preferred embodiments with reference to the following figures, wherein:

FIG. 1 is a schematic drawing of an open bore MRD with the protective sleeve superimposed.

FIG. 2 is a schematic drawing of an open bore MRD with the protective sleeve located within the open bore.

FIG. 3 is a schematic drawing of an open bore MRD with the protective sleeve retracted outside the open bore.

DETAILED DESCRIPTION OF THE INVENTION AND ITS PREFERRED EMBODIMENTS

Figure 4:
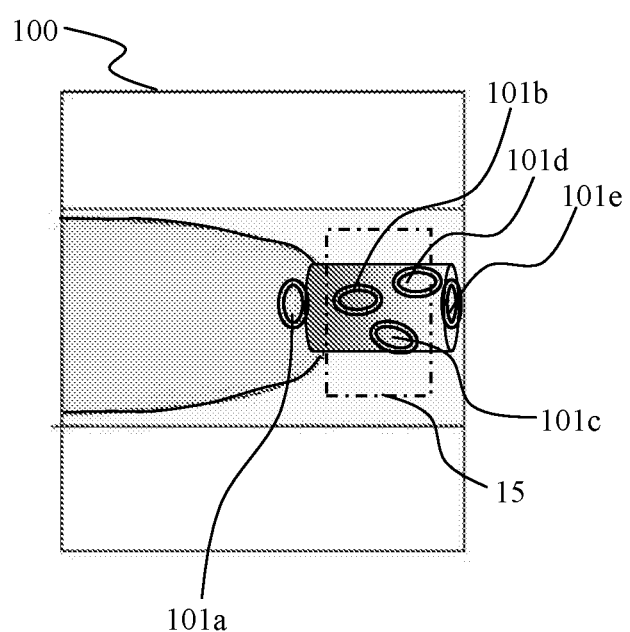
FIG. 4 is a schematic drawing of the protective sleeve configured with at least one movement sensor.

The following description is provided, alongside all chapters of the present invention, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provides means, such as a protective sleeve, and methods for reducing the electromagnetic energy propagation from an MRD's magnet-bore to the outer environment surrounding the magnet, and vice versa The term "MRD" refers herein to a magnetic resonance imaging device.

The term "about" refers herein indicates a value within ±25%.

The term "Faraday shield" refers herein to an enclosure formed by a conducting material or by a mesh of such material, blocking external static and non-static electric fields.

The term "magnetic fringe field" refers herein to spatial gradient magnetic field surrounding the bore of the MRI in three orthogonal magnetic gradients which produces an attractive translational force on ferromagnetic objects. The magnetic in that zone is between 300-5 Gauss and is delimited by a 5-Gauss line. ("zone 4", see FIG. 8 and FIG. 9).

The term "RF" refers hereinafter to radio frequency (RF) in the range of about 3 kHz to 300 GHz.

The term "non-MRD-based motion detector" refers herein to a motion detecting device that is situated separately from a magnetic resonance device.

The term "protective member" refers herein to any embodiment of the protective sleeve mentioned herein.

Reference is now made to FIG. 1, FIG. 2, FIG. 3, and FIG. 4 schematically illustrating in an out-of-scale manner an open bore MRI device (MRD, e.g., an MRI wrist system 100) according to one embodiment of the invention, comprising one or more magnets (here for example, permanent magnet 13) and a volume of interest for imaging a predefined body part and an inlet aperture (11) for inserting a body part within the bore (10), an electrically earthed (21) protective sleeve (20) for reducing the electromagnetic energy propagation from the magnet bore (10) to the outer environment (200) surrounding the MRD (100) and vice versa. A sensor(s)-containing sleeve (20) comprises a distal portion (23) insertably locatable within the bore (10) and a proximal portion (22) attachable to the MRD aperture (11), length and diameter of the sleeve is adapted to accept a non-imaged portion of a body part (32) insertable within the bore (10) whilst the imaged portion (31) protrudes from distal end (23) of sleeve.

The sleeve comprises or connected to one or more sensors (101), at least one sensors' array or a combination thereof, at least one of the sensors is configured to detect, directly or indirectly, movement, acceleration of dislocation of at least one portion or segment of an organ to be scanned or is scanned. At least one sensor is located peripherally a portion of the body to be or is scanned. FIG. 2 illustrates an embodiment where the sleeve is located within the open bore, and FIG. 3 much similarly illustrates another embodiment where the sleeve is located outside the open bore. FIG. 4 illustrates an embodiment where at least one sensor is located in or on, or is in connection with a second sleeve, or a glove-like apparatus, or a dedicated or separated portion or section of the sleeve. Those three embodiments can be co-exist and co-function. Reference is made again to FIG. 4, schematically illustrating a semi-glove like portion, having a plurality of movement sensors, where e.g., sensor 101a is directed towards the palm's root, sensor 101b is located adjacent the palm's middle portion, sensor 101c is facing the thumb and sensor 101d is dedicated to the small finger.

Figure 5:
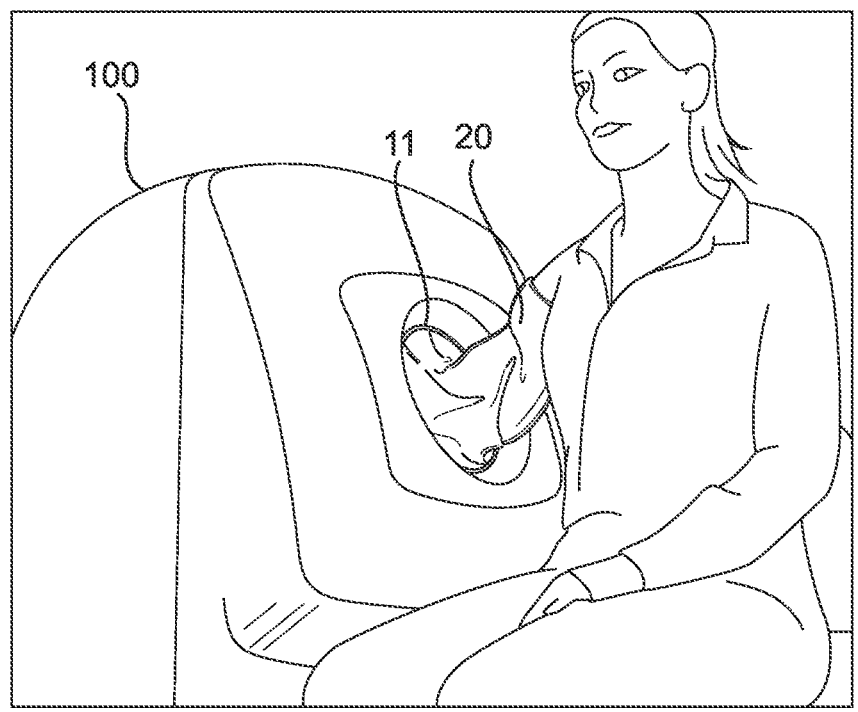
FIG. 5 is a photograph of an open bore MRD in operation.

Reference is now made to FIG. 5 showing a photograph of an open bore MRD (100) according to an example of the aforesaid embodiment of the invention. Sensor-containing sleeve (20, located outside the MRD's open bore) protrudes outside the MRD's inner bore and is connected to bore's inlet aperture (11).

Figure 6:
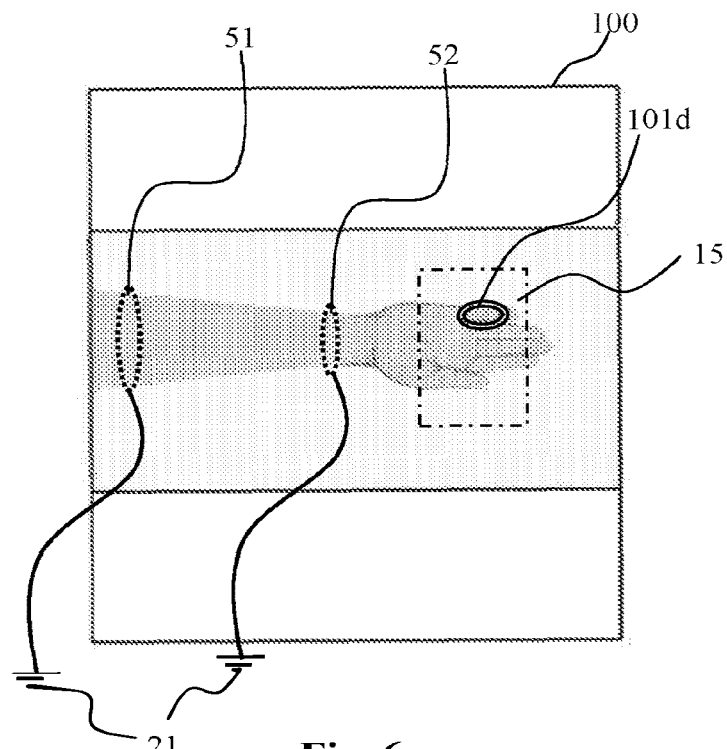
FIG. 6 is a side-view schematic drawing of an open bore MRD as another embodiment of the invention.

Reference is now made to FIG. 6, schematically illustrating an out-of-scale manner a side view of an MRD (100) according to yet another embodiment of the invention. The MRD having a volume of interest (15) for imaging a body part and one or more electrically earthed (21) protective members (51, 52), such a sleeves, dresses, bands, bracelets, collars, tourniquet, tags, clips etc., each of which is made of MRI safe materials, such as copper and electrically conducting polymers. The protective members are provided useful for reducing the electromagnetic energy propagation from MRD (100) to the outer environment surrounding the MRD and vice versa. Properties of members 51 and 52, such as length and diameter are set as a function of the dimensions of the portion of body to be analyzed. It is in the scope of the invention wherein two or more protective members are interconnected by means of electrically conductive materials. Sensor 101d for example is located within the volume.

Figure 7:
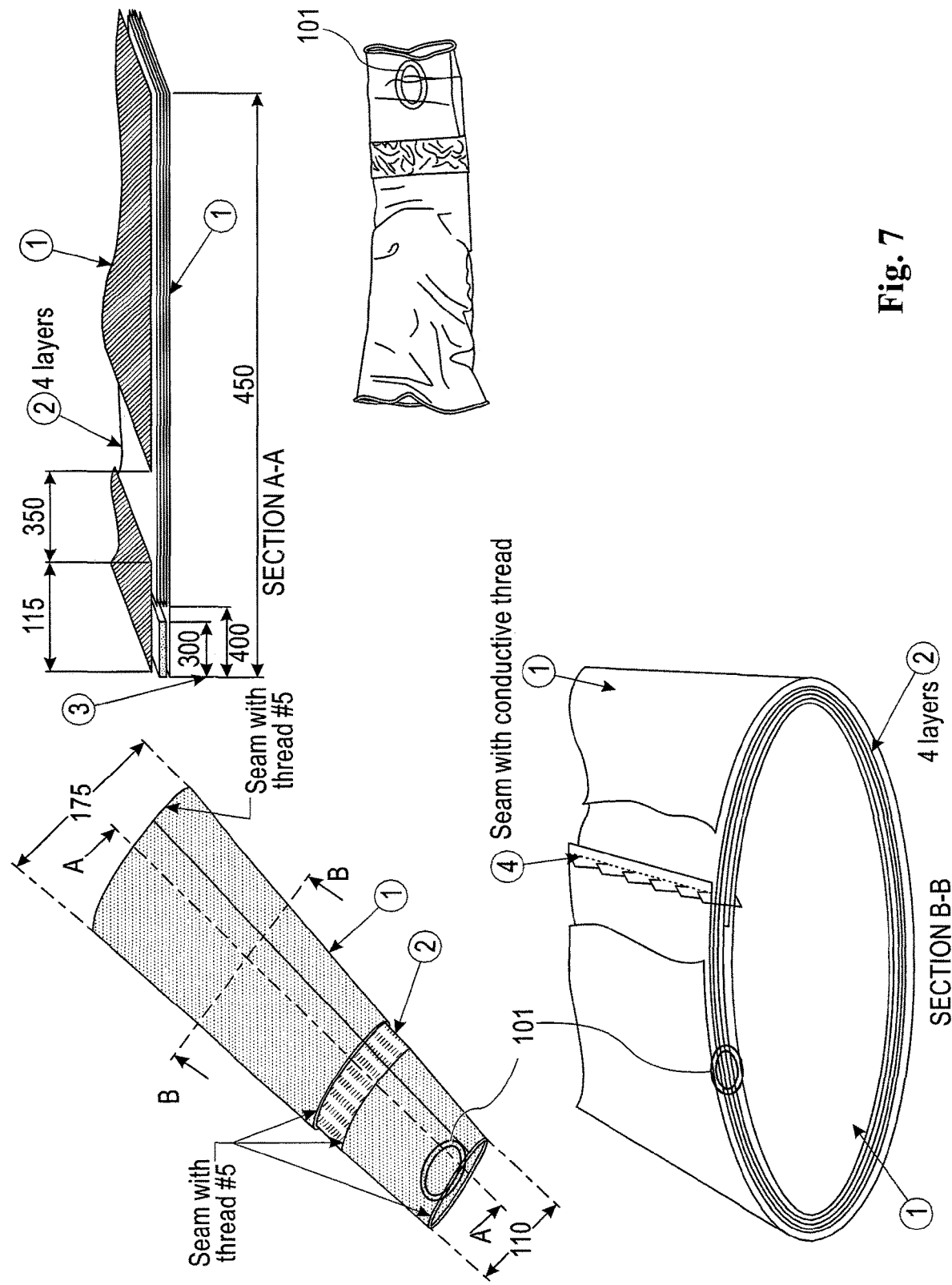
FIG. 7 is a schematic drawing illustrating sections of the protective sleeve in one embodiment.
Figure 8:
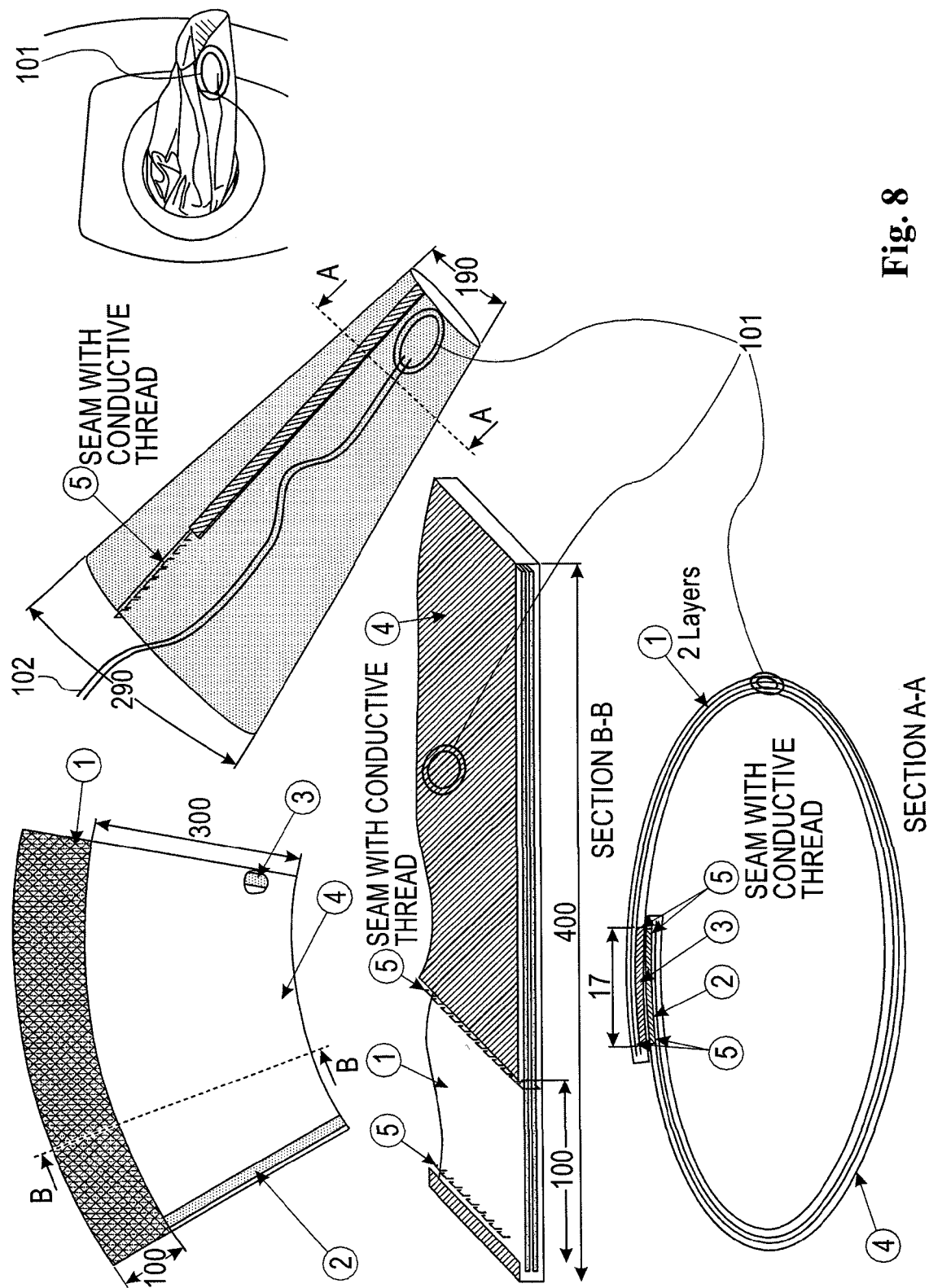
FIG. 8 is a schematic drawing illustrating sections of the protective sleeve in one embodiment.

Reference is now made to FIG. 7 and FIG. 8, schematically illustrating sections and portions of a tourniquet-like protective sensor-containing sleeve (20). In this example, sleeve (20) comprises a copper net or a layer comprising any other electrically conductive materials (1), an electrically conductive hook (2), an electrically conductive loop (3), a fabric sleeve (4), a conductive thread (5), an outer conducting strip (6) for connection to an external protective earthing system; and a fastening means (7). Sensor 101 is located in a distal portion of the sleeve. In addition, according to an embodiment of the technology, sensor 101 is communicate with its correlated medical and MRI systems and subsystems via or by means of a communication pathway 102, such as, for example MRI-safe, wired channel or MRI-safe wireless networking facilities.

Figure 9:
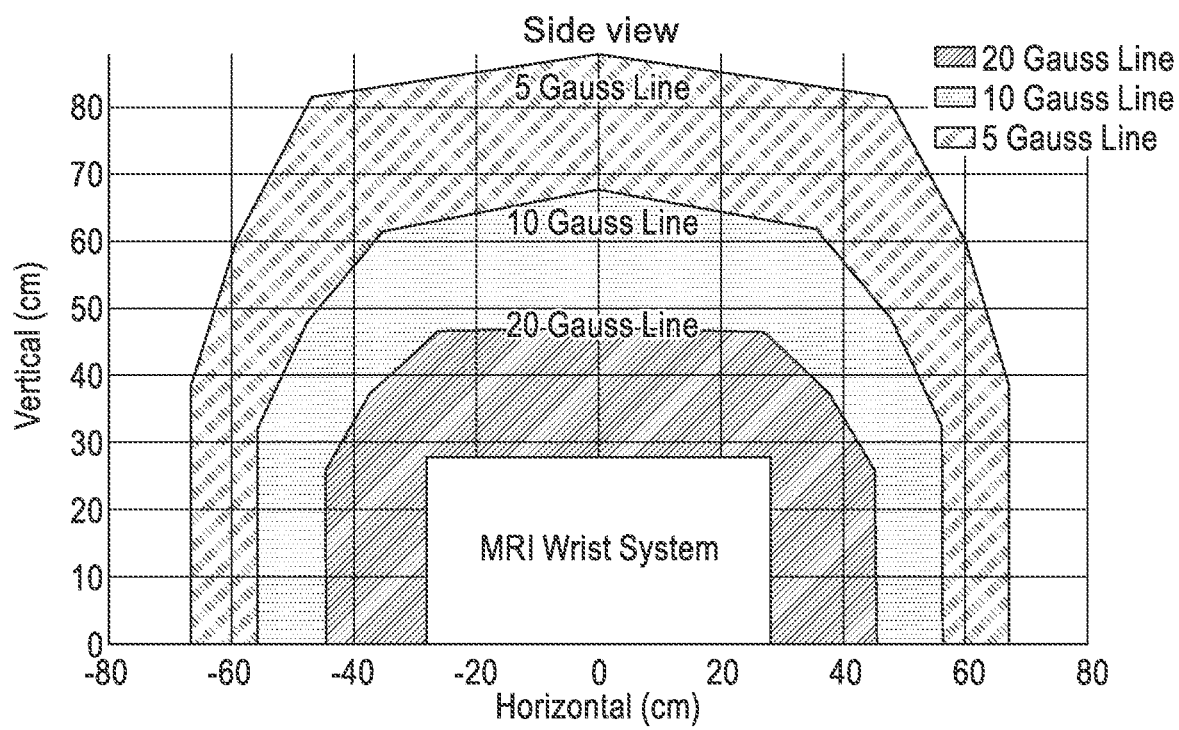
FIG. 9 is a side-view schematic illustrating electromagnetic shielding qualities of the protective sleeve.
Figure 10:
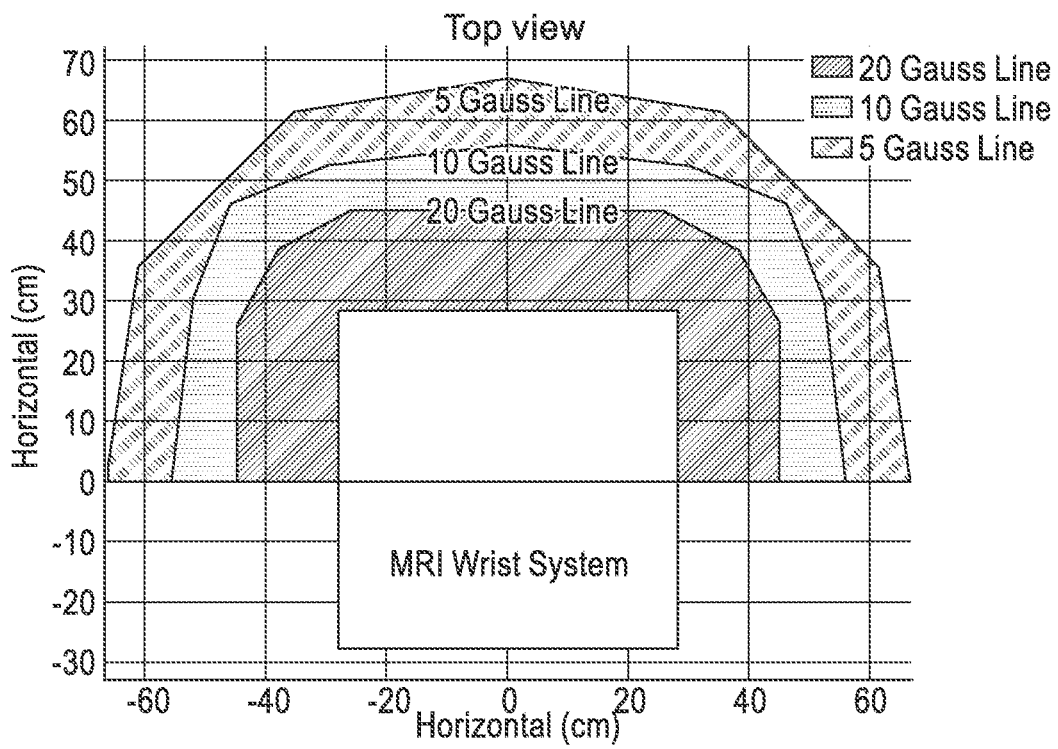
FIG. 10 is a top-view schematic illustrating electromagnetic shielding qualities of the protective sleeve.

Reference is now made to FIG. 9 and FIG. 10, schematically illustrating a side view and top view, respectively, of Fringe filed 5 Gause line of an M2 type MRI by Aspect Imaging Ltd (IL) in connection with a protective sleeve (MRI wrist system) according to the second embodiment of the invention.

It is in the scope of the invention wherein the conductive material is a copper net or an electrically conductive layer thereof. It is further in the scope of the invention wherein the electrically conductive materials are selected, in a non-limiting manner from a group consisting of non-magnetic, electrical conductor, such as copper, silver, or aluminum, conductive polymers, such as polyacetylene, polyaniline, polypyrrole, polythiophene, and polyphenylene; synthetic or non-synthetic fibers which comprise carbon derivatives such as carbon nanotubes, carbon black, graphite; fabrics incorporated with inorganic conductive materials, tin oxide, copper sulfide, nickel graphite and any combination thereof.

It is further in the scope of the invention wherein the electrically conductive material or layer thereof is in the form of a mesh or a knitted fabric such that the mesh size is significantly smaller than the wavelengths to be reflected. It is further in the scope of the invention wherein the protective member comprises at least one of the following: layer of fabric or textile such as cotton, polyester, nylon and silk, high-performance fibers including Kevlar®, Nomex®, Technora® and Vectran®, for close-fitting on the cylindrical organ. It is further in the scope of the invention wherein two or more layers of fabric are in fluid connection to a fluid source and pump, positioned to entrap a fluid therein, thereby providing expansion of the fabric sleeve to fit dimensions of the organ in a tourniquet-like manner. It is further in the scope of the invention wherein the protective member is designed to provide an effective insulation for non-imaged body extremities. It is further in the scope of the invention wherein the electrically conductive loop is connected to the protective earthing terminal in a way that they cannot be separated without the aid of a tool, according to IEC 60601-1-2 Medical Electrical Equipment standards. It is further in the scope of the invention wherein RF field effects are caused by one or more of the following: external RF such as radio waves from the vicinity of the MRD suite and RF electromagnetic radiation produced by nuclear relaxation inside the subject or internal RF from the radio frequency transmission system of the MRD, or any combination thereof. It is further in the scope of the invention wherein the protective member provides an effective Faraday shielding thus performing as a barrier to prevent entry of external RF from the environment of the MRD to the MRD's bore and vice versa.

In one example, yet still in a non-limiting manner, a protective member as shown in any of the embodiments illustrated and disclosed above, effectively reduces internal RF field effects within the MRD's bore at frequencies of about 100 MHz, and eliminate ohmic tissue heating, heating of conductors, and interference with patient monitoring equipment; and vice versa, the protective gear reduces external RF field effects of the environment of the MRD to penetrate the inner bore and VOI of the MRD.

In another example, provided herein still in a non-limiting manner, a protective member as shown in any of the embodiments illustrated and disclosed above, effectively eliminates tissue heating due to RF magnetic fields during MR scanning, and limits temperature rises in excess of 1° C. and localized heating up to 38° C. in the head, 39° C. in the trunk, and 40° C. in the extremities.

In another example, provided herein still in a non-limiting manner, a protective member as shown in any of the embodiments illustrated and disclosed in above, effectively maintains SAR levels below recommended limits as follows: 4 Watt/kg averaged over the whole body for any 15-minute period (1.5 Watt/kg if the patient is thermally compromised, as a function of room temperature and humidity), 3.2 Watt/kg averaged over the head for any 10-minute period, and 8 W/Kg in any 1 cc of tissue in head averaged over 5 minutes.

In another example, provided herein still in a non-limiting manner, a protective member as shown in any of the embodiments illustrated and disclosed above, effectively maintains the magnetic fringe field strength at the entrance to the MRI suite to be equal to or less than 5 Gauss, referred to as "the 5-Gauss line."

In another example, provided herein still in a non-limiting manner, a protective member as shown in any of the embodiments illustrated and disclosed above, effectively prevents temperature rises due to RF heating during MR scanning beyond the limit of 40° C. in the body extremity.

In another example, provided herein still in a non-limiting manner, a protective member as shown in any of the embodiments illustrated and disclosed above, is adapted to fit one or more of the body extremities such as a toe, finger, wrist, elbow, ankle, knee, or head, as well as body non-extremities, such as the abdomen, belly, etc, and any combination thereof.

In another example, provided herein still in a non-limiting manner, a protective member as shown in any of the embodiments illustrated and disclosed above, is adapted to provide a separation means for preventing skin-to-skin contact of body parts selected from the group comprising inner thigh-to-thigh, calf-to-calf, hand-to-hand, hand-to-body, ankle-to-ankle contact, thereby preventing the formation of conductive loops through part of the body.

In another example, provided herein still in a non-limiting manner, a protective member as shown in any of the embodiments illustrated and disclosed above, is adapted to provide a means for preventing the placement of the body extremity against an RF transmitting coil surface.

In another example, provided herein still in a non-limiting manner, a protective member as shown in any of the embodiments illustrated and disclosed above, is adapted to provide SAR conforming to NEMA MS-8-2006 for MRI Systems.

In another example, provided herein still in a non-limiting manner, a protective member as shown in any of the embodiments illustrated and disclosed above, is adapted to adapted to fit an orifice of a body therein.

In another example, provided herein still in a non-limiting manner, a protective member as shown in any of the embodiments illustrated and disclosed above, comprises a sleeve-like. organ-accommodating article of manufacture. The article comprises: a fabric sleeve (1); an intermediate conducting layer (2); an outer dielectric layer (3) an outer conducting strip (4); wherein the fabric sleeve is adjusted to accommodate a body extremity; the intermediate conducting layer is placed/sewn or otherwise surrounds the fabric sleeve; the outer dielectric layer is placed/sewn or otherwise surrounds the intermediate conducting layer; and the outer conducting strip is fastened to the outer dielectric layer with at least one contact with the intermediate conducting layer and at least one contact to an external earthing system (5).

In another example, provided herein still in a non-limiting manner, a protective member as shown in any of the embodiments illustrated and disclosed above, applies with Electrical & Mechanical Safety (IEC 60601-1)General requirements for basic safety and essential performance.

In another example, provided herein still in a non-limiting manner, a protective member as shown in any of the embodiments illustrated and disclosed above is configured in compliance with Electromagnetic Compatibility (IEC 60601-1-2) General requirements for basic safety and essential performance—Collateral standard: Electromagnetic compatibility—Requirements and tests.

In another example, provided herein still in a non-limiting manner, a protective member as shown in any of the embodiments illustrated and disclosed above is configured in compliance with IEC 60601-2-33 Medical electrical equipment—Part 2-33: Particular requirements for the basic safety and essential performance of magnetic resonance equipment for medical diagnostic (2007 (Second Edition)+A1:2005+A2:2007).

In another example, provided herein still in a non-limiting manner, a protective member as shown in any of the embodiments illustrated and disclosed above, above is configured in compliance with the NEMA MS 4 (2010) Acoustic Noise Measurement Procedure for Diagnosing Magnetic Resonance Imaging Devices In another example, provided herein still in a non-limiting manner, a protective member as shown in any of the embodiments illustrated and disclosed above, is configured in compliance with NEMA MS 8 (2006) Characterization of the Specific Absorption Rate (SAR) for MRI Systems.

In another example, provided herein still in a non-limiting manner, a protective member as shown in any of the embodiments illustrated and disclosed above, is configured in compliance with NEMA MS 10-2006 Determination of Local Specific Absorption Rate (SAR) in Diagnostic Magnetic Resonance Imaging.

In another example, provided herein still in a non-limiting manner, a protective member as shown in any of the embodiments illustrated and disclosed above, is configured in compliance with NEMA MS 11-2006 Determination of Gradient-Induced Electric Fields in Diagnostic Magnetic Resonance Imaging.

In another example, provided herein still in a non-limiting manner, a protective member as shown in any of the embodiments illustrated and disclosed above, is configured in compliance with IEC 60601-2-33 Medical electrical equipment—Part 2-33: Particular requirements for the basic safety and essential performance of magnetic resonance equipment for medical diagnostic (2007 (Second Edition)+A1:2005+A2:2007).

It is thus an object of the current invention to disclose a first method for avoiding object motion artifacts during MRI imaging. The method comprising steps of: (a) providing a movement sensor in or in connection with a RF protective/immobilizing sleeve, (b) acquiring a sequence of N MRI consecutive images $CI_n$ of an object; (c) storing on a computer readable medium (CRM) at least one parameter p indicating spatial image orientation at which the image was taken for each $CI_n$; (d) analyzing the sequence of the $CI_n$ for detection of the object movement; (e) tagging $K_M$ images $CI_k^M$ of at least one movement M of the object; and (f) determining, using the tagged images $CI_k^M$ for each of movement M, the following parameters: (i) two of the following: the movement starting time $T_{MS}$, the movement ending time $T_{ME}$, and time length of the movement $T_M$; and (ii) the movement spatial image orientation parameter $P_{MS}$ at the beginning of the movement, wherein the method additionally comprises, for each M whose $T_M$ is shorter than a predetermined time length PT, steps of acquiring a sequence of $K_M$ MRI consecutive images $NCI_k^M$ starting at the $P_{MS}$; and ending after the $T_M$; replacing the $NCI_k^M$ with the $CI_k^M$ in the sequence; repeating steps (c)-(f) until no more movements whose $T_M$ is shorter than the PT are detected; thereby producing an image sequence with reduced object-movement in MRI imaging. The method thus enhances the quality of the MRI images acquired, increases SNR, and decreases associated artifacts.

It is another object of the current invention to disclose a second method for reducing the effect of object movements during MRI imaging; the method comprising steps of: (a) providing a movement sensor in or in connection with a RF protective/immobilizing sleeve; (b) acquiring a sequence of N MRI consecutive images $CI_n$ of an object; (c) storing on a computer readable medium (CRM) at least one parameter p indicating spatial image orientation at which the image was taken for each $CI_n$; (d) analyzing the motion of the object by means of one or more non-MRD-based motion detectors; (e) tagging $K_M$ images $CI_k^M$ of at least one movement M of the object; and (f) determining, using the tagged images $CI_k^M$ for each of movement M, the following parameters: (i) two of the following: the movement starting time $T_{MS}$, the movement ending time $T_{ME}$, and time length of the movement $T_M$; and (ii) the movement spatial image orientation parameter $P_{MS}$ at the beginning of the movement, wherein the method additionally comprises, for each M whose $T_M$ is shorter than a predetermined time length PT, steps of acquiring a sequence of $K_M$ MRI consecutive images $NCI_k^M$ starting at the $P_{MS}$; and ending after the $T_M$; replacing the $NCI_k^M$ with the $CI_k^M$ in the sequence; repeating steps (c)-(f) until no more movements whose $T_M$ is shorter than PT are detected; thereby producing an image sequence with reduced Object-movement in MRI imaging.

It is another object of the current invention to disclose a method for reducing the effect of object movements during MRI imaging as defined in any of the above, additionally comprising a step of selecting the non-MRD-based motion detectors from a group consisting of or otherwise comprising: passive infrared sensors; detectors which senses body heat; mechanical detector; electronic detectors; optical detectors; acoustical detectors; sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors (triboelectric, seismic, and inertia-switch sensors); and any combination thereof.

It is another object of the current invention to disclose a method as defined in any of the above, wherein the method additionally comprises the step of selecting the parameter from a group consisting of: angle of image with respect to the object, spatial coordinates of the area of the image, location of MRI components and a combination thereof.

It is another object of the current invention to disclose a method as defined in any of the above, wherein the method additionally comprises the step of selecting the object from a group consisting of: adult person, person under anesthesia, infant, premature baby, animal and a combination thereof.

It is another object of the current invention to disclose a method as defined in any of the above, wherein the method additionally comprises the step of characterizing at least one movement M by the extent of the movement.

It is another object of the current invention to disclose a method as defined in any of the above, wherein the method additionally comprises an image processing step prior to step (c); wherein the processing step comprising performing Fourier transformation on the consecutive image to momentum space (K-space).

It is another object of the current invention to disclose a method as defined in any of the above, wherein the step of analyzing is performed on images in K-space.

It is another object of the current invention to disclose an MRI system imaging a movable object. The MRI system comprising: providing a movement sensor in or in connection with an RF protective/immobilizing sleeve, an MRI device adapted to take a sequence of N MRI consecutive images $CI_n$ of an object; each of the images is characterized by at least one parameter p indicating spatial image orientation at which image was taken; a computer readable medium (CRM) in communication with the MRI; the CRM having instructions thereon for executing a method comprising steps of: analyzing the sequence of $C_n$; and tagging thereby $K_M$ images $CI_k^M$ of at least one movement M of the object; for each movement M, determining the following using the tagged images $CI_k^M$: (a) two of the following: the movement starting time $T_{MS}$, the movement ending time $T_{ME}$, and time length of the movement $T_M$; and (b) the movement spatial image orientation parameter $P_{MS}$ at the beginning of the movement; wherein for each M whose $T_M$ is shorter than a predetermined time length PT, the instructions are additionally adapted for acquiring a sequence of $K_M$ MRI consecutive images $NCI_k^M$, starting at the $P_{MS}$ and ending after $T_M$; replacing the $NCI_k^M$ with $CI_k^M$ in the sequence; and repeating steps (i)-(iv) until no more movements whose $T_M$ is shorter than PT are detected.

It is another object of the current invention to disclose an MRI system imaging a movable object as defined in any of the above, wherein the non-MRD-based motion detectors are selected from a group consisting of or otherwise comprising: passive infrared sensors; detectors which senses body heat; mechanical detector; electronic detectors; optical detectors; acoustical detectors; pressure detectors, location or dislocation sensors, sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors (triboelectric, seismic, and inertia-switch sensors); and any combination thereof.

It is another object of the current invention to disclose an MRI system imaging a movable object as defined in any of the above, wherein the parameter is selected from a group consisting of: angle of image with respect to the object, spatial coordinates of the area of the image, location of MRI components and a combination thereof.

It is another object of the current invention to disclose an MRI system imaging a movable object as defined in any of the above, wherein the object is selected from a group consisting of: adult person, person under anesthesia, infant, premature baby, animal and a combination thereof.

It is another object of the current invention to disclose an MRI system imaging a movable object as defined in any of the above, wherein the at least one movement M is characterized by extent of the movement.

It is another object of the current invention to disclose an MRI system imaging a movable object as defined in any of the above, wherein the system instructions additionally perform a Fourier transformation on the consecutive image to momentum space (K-space) prior to the analysis.

It is another object of the current invention to disclose an MRI system imaging a movable object as defined in any of the above, wherein the analysis is performed on images in K-space.

The following description is provided so as to enable any person skilled in the art to make use of the invention and sets forth examples contemplated by the inventor of carrying out this invention. Various modifications, however, will remain apparent to those skilled in the art, since the generic principles of the present invention have been defined specifically. Also, it is to be understood that the phraseology and terminology employed herein is for the purpose of description and should not be regarded as limiting.

Figure 11:
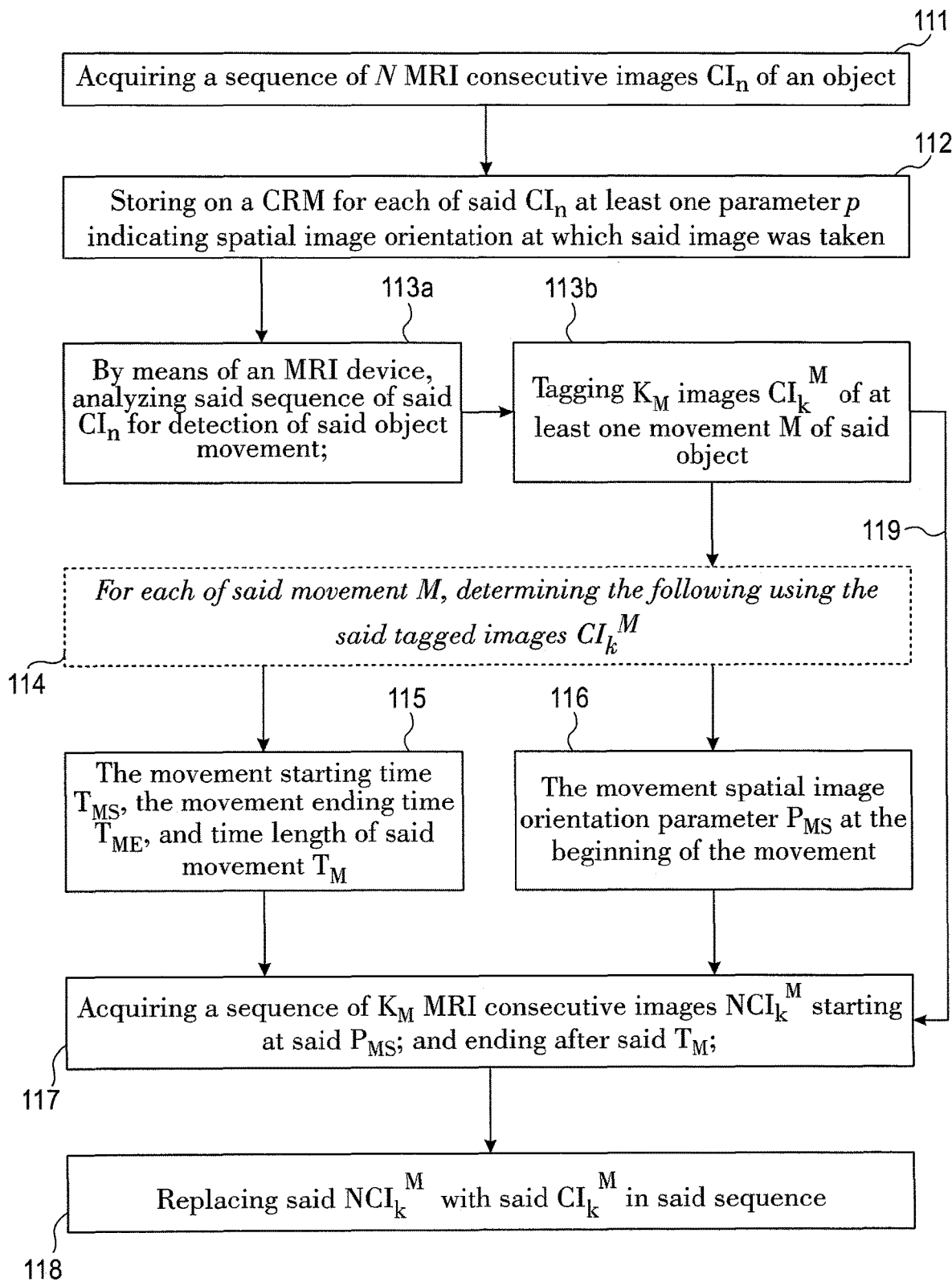
FIG. 11 is a flow chart schematic of the method of reducing the effects of object motion on the MRI imaging data.

According to one embodiment of the present invention, a first method for reducing the effect of object movements during MRI imaging is disclosed. Reference is now made to FIG. 11, presenting an embodiment, which is based on an MRD-based motion detector (See step 113A), of such a method which inter alia comprises the following steps: (a) acquiring a sequence of N MRI consecutive images $CI_n$ of an object (111); (b) storing on a computer readable medium (CRM) at least one parameter p indicating spatial image orientation at which the image was taken for each $CI_n$ (112); (c) analyzing (113A) the sequence of $C_n$ for detection of the object movement; (d) tagging (113B) $K_M$ images $CI_k^M$ of at least one movement M of the object; (e) determining (114), using said tagged images $CI_k^M$ for each of movement M, the following parameters: (i) two of the following: the movement starting time $T_{MS}$, the movement ending time $T_{ME}$, and time length (115) of the movement $T_M$; and (ii) the movement spatial image orientation parameter (116) $P_{MS}$ at the beginning of the movement, wherein the method additionally comprises, for each said M whose $T_M$ is shorter than a predetermined time length PT, steps of acquiring a sequence of $K_M$ MRI consecutive images $NCI_k^M$ (117), starting at said $P_{MS}$ and ending after $T_M$; replacing $NCI_k^M$ with $CI_k^M$ in the sequence; repeating steps (b)-(e) (119) until no more movements whose $T_M$ is shorter than PT are detected; thereby, producing an image sequence with reduced object-movement in MRI imaging (118).

Figure 12:
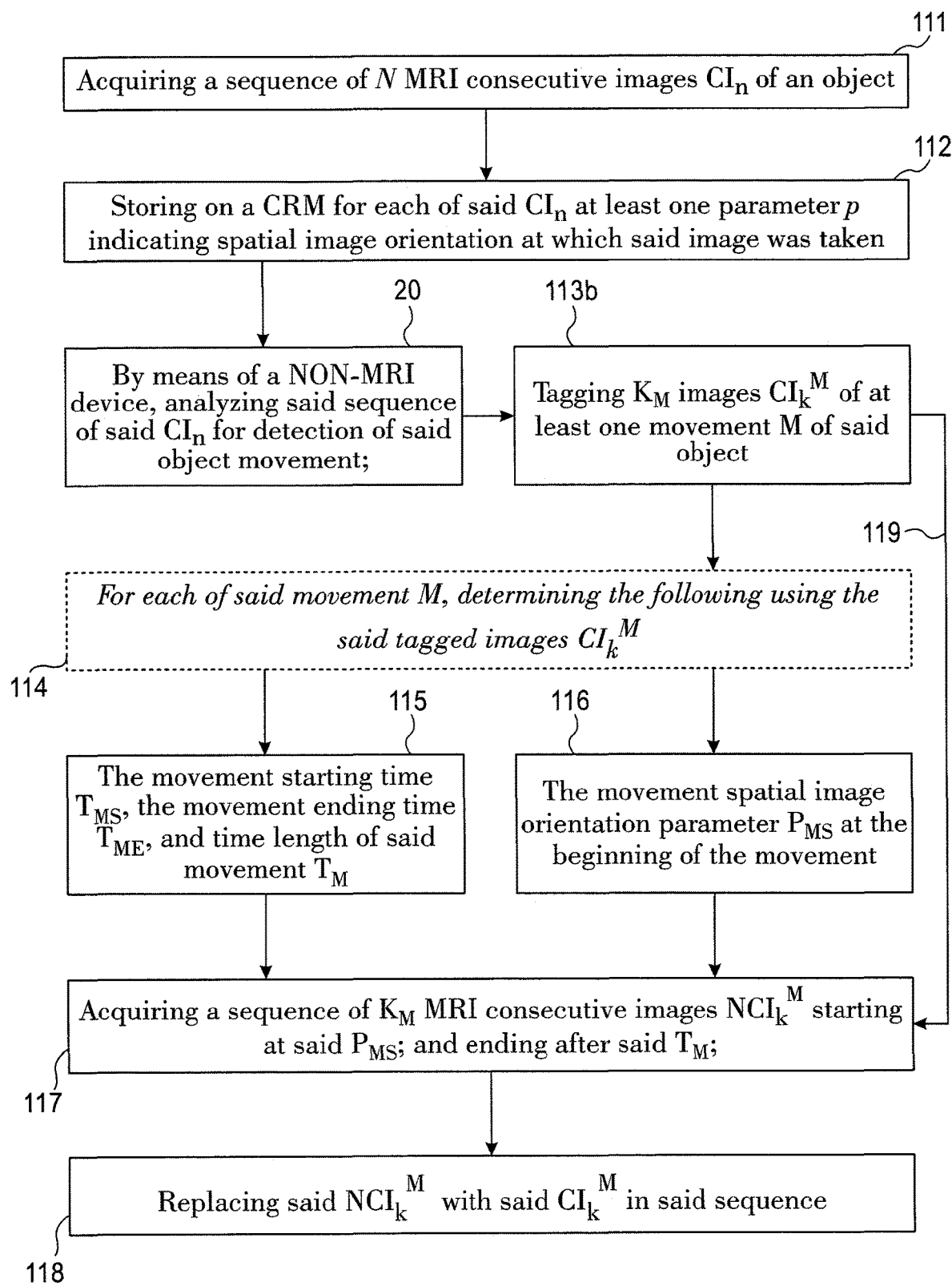
FIG. 12 is a flow chart schematic of the method of reducing the effects of object motion on the MRI imaging data.

According to another embodiment of the present invention, a first method for reducing the effect of object movements during MRI imaging is disclosed. Reference is now made to FIG. 12, presenting an embodiment, based on a NON-MRD-BASED motion detector (See step 120), of such a method which inter alia comprises the following steps: (a) acquiring (111) a sequence of N MRI consecutive images $C_n$ of an object; (b) storing on a computer readable medium (CRM) at least one parameter p indicating spatial image orientation at which the image was taken for each $CI_n$; (c) analyzing (120) motion of the object by means of one or more non-MRD-based motion detectors; (d) tagging (113B) thereby $K_M$ images $CI_k^M$ of at least one movement M of the object; (e) determining (114), using said tagged images $CI_k^M$ for each of movement M, the following parameters: (i) two of the following: the movement starting time $T_{MS}$, the movement ending time $T_{ME}$, and time length (115) of the movement $T_M$; and (ii) the movement spatial image orientation parameter $P_{MS}$ (116) at the beginning of the movement, wherein the method additionally comprises, for each M whose $T_M$ is shorter than a predetermined time length PT, steps of acquiring (117) a sequence of $K_M$ MRI consecutive images $NCI_k^M$, starting at the $P_{MS}$ and ending after $T_M$; replacing $NCI_k^M$ with $CI_k^M$ in the sequence; repeating (119) steps (c)-(f) until no more movements whose $T_M$ is shorter than PT are detected; thereby, producing (118) an image sequence with reduced object-movement in MRI imaging.

Figure 13A:
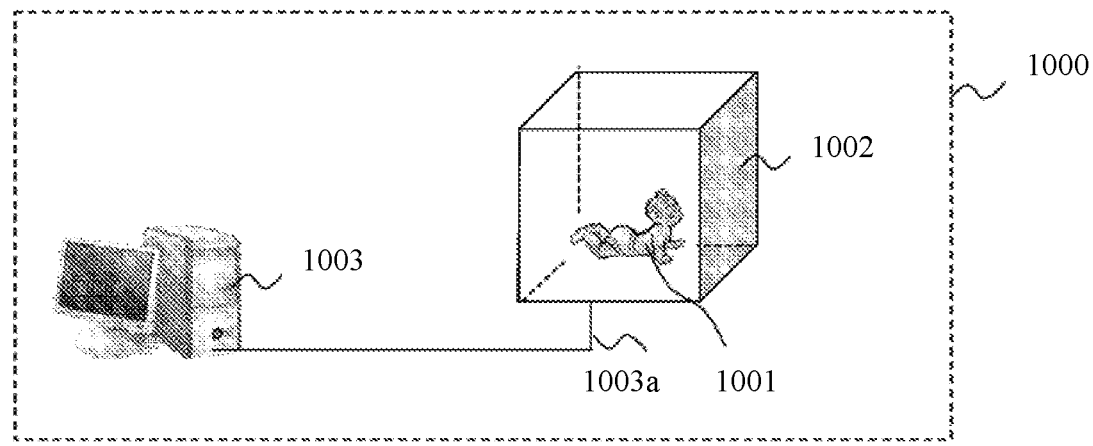
FIG. 13a is a conceptual representation of an embodiment of the invention with a MRD-based motion detector.

According to another embodiment of the present invention, a first MRI imaging system, adapted for reducing the effect of object movements during MRI imaging is disclosed. Reference is now made to FIG. 13A, presenting an embodiment of MRI imaging system (1000), having an MRD-based motion detector, of such a system which inter alia comprises the following modules: an MRI device (1002) adapted to take a sequence of N MRI consecutive images $C_n$ of an object (1001); each of the images is characterized by at least one parameter p indicating spatial image orientation at which the image was taken; a computer readable medium (CRM, 1003) in communication (1003A) with the MRI; the CRM having instructions thereon for executing a method comprising steps of: (a) analyzing the sequence of $CI_n$; (b) tagging thereby $K_M$ images $CI_k^M$ of at least one movement M of the object; (c) determining, using said tagged images $CI_k^M$ for each of movement M, the following parameters: (i) two of the following: the movement starting time $T_{MS}$, the movement ending time $T_{ME}$, and time length of the movement $T_M$; and (ii) the movement spatial image orientation parameter $P_{MS}$ at the beginning of the movement; wherein for each M whose $T_M$ is shorter than a predetermined time length PT, the instructions are additionally adapted for acquiring a sequence of $K_M$ MRI consecutive images $NCI_k^M$, starting at the $P_{MS}$ and ending after $T_M$; replacing $NCI_k^M$ with $CI_k^M$ in the sequence; and repeating steps (a)-(c) until no more movements whose $T_M$ is shorter than PT are detected.

Figure 13B:
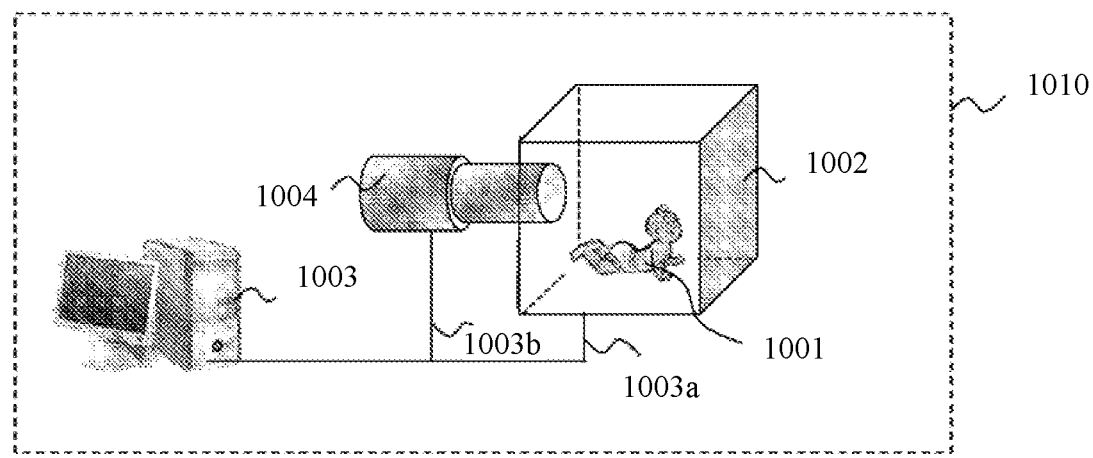
FIG. 13b is a conceptual representation of an embodiment of the invention with a non-MRD-based motion detector.

According to yet another embodiment of the present invention, a second MRI imaging system (1010), adapted for reducing the effect of object movements during MRI imaging is disclosed. Reference is now made to FIG. 13B, presenting an embodiment of MRI imaging system (1001), having a NON-MRD-BASED motion detector (See 1004), of such a system which inter alia comprises the following modules: an MRI device (1002) adapted to take a sequence of N MRI consecutive images $CI_n$ of an object (1001); each of said images is characterized by at least one parameter p indicating spatial image orientation at which said image was taken; a computer readable medium (CRM, 1003) in communication (1003A) with said MRL MRI system 101 further comprises one or more NON-MRD-BASED motion detector (1004) in communication (1003B) with said CRM (1003), CRM (1003) having instructions thereon for executing a method comprising steps of: (a) analyzing said sequence of said $CI_n$; (b) tagging thereby $K_M$ images $CI_k^M$ of at least one movement M of said object; and (c) determining, using said tagged images $CI_k^M$ for each of movement M, the following parameters: (i) two of the following: the movement starting time $T_{MS}$, the movement ending time $T_{ME}$, and time length of said movement $T_M$; and (ii) the movement spatial image orientation parameter $P_{MS}$ at the beginning of the movement; wherein for each said M, whose $T_M$ is shorter than a predetermined time length PT, said instructions are additionally adapted for acquiring a sequence of $K_M$ MRI consecutive images $NCI_k^M$, starting at the $P_{MS}$ and ending after $T_M$; replacing $NCI_k^M$ with $CI_k^M$ in the sequence; and repeating steps (a)-(c) until no more movements whose $T_M$ is shorter than PT are detected.

The MRI devices and methods as disclosed in any of the above are all targeted for avoiding or eliminating or otherwise reducing motion artifacts. These devices and methods are useful for producing an image sequence characterized by reduced object-movement effects. These devices are adapted to image uncontrollably movable objects, such as neonates, premature babies and laboratory animals; and especially to image motion-artifacts free images in relevant medical or research cases were restrain of the object is to be avoided (e.g., neonates clinical examination) or impossible (e.g., lab animals imaging for research).

What is claimed:

1. A protective sleeve for reducing electromagnetic energy propagation from a magnet bore of a magnetic resonance imaging (MRI) device to a surrounding environment and for reducing electromagnetic energy propagation from the surrounding environment into said magnet bore, said protective sleeve comprising:
   a distal portion configured to be insertably locatable within the magnet bore and extractably locatable from within the magnet bore to outside the magnet bore;
   a proximal portion attachable to an inlet aperture of the magnet bore, wherein:
      the protective sleeve is configured to accept a body part for insertion within the magnet bore; and
      the distal portion of the protective sleeve is configured such that upon insertion of the body part into the protective sleeve in such a manner to cause the distal portion to be located within the magnet bore, the body part is located within the magnet bore with a first portion of the body part protruding from the distal portion of the protective sleeve into a volume of interest of the MRI device, and a second portion of the body part remaining within the distal portion of the protective sleeve;
   and
   one or more sensors configured to detect, directly or indirectly, one or more of movement, acceleration or dislocation of the first portion of the body part.

2. The protective sleeve of claim 1, wherein:
said protective sleeve comprises a fabric sleeve, an intermediate conducting layer, an outer dielectric layer and an outer conducting strip having a first contact and a second contact,
said fabric sleeve is configured to accommodate the body part,
said intermediate conducting layer surrounds said fabric sleeve,
said outer dielectric layer surrounds said intermediate conducting layer, and
the first contact of said outer conducting strip is fastened to the outer dielectric layer and the second contact is operably couplable to an external earthing system.

3. The protective sleeve of claim 1, wherein said protective sleeve is configured to:
effectively eliminate tissue heating due to radiofrequency magnetic fields during magnetic resonance scanning,
limit temperature rises in excess of 1° C. and localized heating to 38° C. in a head, 39° C. in a trunk, and 40° C. in extremities, and
maintain Specific Absorption Rate (SAR) levels below recommended limits as follows: 4 Watt/kg averaged over the whole body for any 15-minute period or 1.5 Watt/kg if the patient is thermally compromised, as a function of room temperature and humidity, 3.2 Watt/kg averaged over the head for any 10-minute period, and 8 W/Kg in any 1 cc of tissue in the head averaged over 5 minutes.

4. The protective sleeve of claim 1, wherein said protective sleeve is configured to effectively limit a magnetic fringe field at an entrance of an MRI suite containing the MRI device to 5 Gauss or less.

5. The protective sleeve of claim 1, wherein said protective sleeve is configured to effectively prevent temperature rises due to radiofrequency heating during magnetic resonance scanning, beyond 40° C. in said body part.

6. The protective sleeve of claim 1, wherein the body part includes one or more body extremities and one or more body non-extremities.

7. The protective sleeve of claim 6, wherein the one or more body extremities include one or more of a toe, a finger, a wrist, an elbow, an ankle, a knee, and a head.

8. The protective sleeve of claim 6, wherein the one or more body non-extremities include one or more of an abdomen and a belly.

9. The protective sleeve of claim 1, wherein said protective sleeve is configured to provide separation means for preventing skin-to-skin contact of body parts including inner thigh-to-thigh contact, calf-to-calf contact, hand-to-hand contact, hand-to-body contact, and ankle-to-ankle contact, thereby preventing the formation of conductive loops through part of the body.

10. The protective sleeve of claim 1, wherein said protective sleeve is configured to provide a means for preventing the placement of said body part against a radiofrequency transmitting coil surface.

11. The protective sleeve of claim 1, wherein said protective sleeve is adapted to fit an orifice of a body therein.

12. The protective sleeve of claim 1, wherein the one or more sensors comprise at least one sensor array.

13. The protective sleeve of claim 1, wherein at least one of the one or more sensors is located at a position on the protective sleeve such that upon insertion of the body part into the protective sleeve, the position is peripheral to the first portion of the body part.

14. A magnetic resonance imaging (MRI) system comprising:
an MRI device having a magnet bore, a computer readable medium (CRM), and a processor, wherein the magnet bore includes an inlet aperture; and
the protective sleeve of claim 1 wherein the proximal portion of the protective sleeve is attached to the inlet aperture of the magnet bore of the MRI device,
wherein:
the MRI device and the processor are adapted to produce a sequence of N MRI consecutive images ($CI_n$ sequence) of the first portion of the body part, each of said images is characterized by at least one parameter p indicating spatial image orientation at which said image was taken, and
the CRM in communication with said processor; said CRM having instructions thereon such that when executed by the processor, cause the processor to:
(a) detect movement M of the first portion of the body part based on the one or more sensors;
(b) for each detected movement M:
(i) analyze said $CI_n$ sequence to find and tag a corresponding sequence of $K_M$ images ($CI_k^M$ sequence) that were taken during said movement M;
(ii) determine, using said $CI_k^M$ sequence:
(A) at least one of: a movement starting time ($T_{MS}$) and a movement ending time ($T_{ME}$);
(B) a time length of said movement ($T_M$); and
(C) a movement spatial image orientation parameter ($P_{MS}$) at a beginning of the detected movement M; and
(c) when $T_M$ is shorter than a predetermined time length (PT):
(i) acquire a sequence of $K_M$ MRI consecutive images ($NCI_k^M$ sequence) starting at said $P_{MS}$ and ending after said $T_M$; and
(ii) replace said $CI_k^M$ sequence with said $NCI_k^M$ sequence in said $CI_n$ sequence.

15. The MRI system of claim 14, wherein the one or more sensors include one or more: passive infrared sensors; detectors which sense body heat; mechanical detectors; electronic detectors; optical detectors; acoustical detectors; pressure detectors; location or dislocation sensors; sound detectors including acoustic sensors; opacity detectors including optical and infrared sensors and video image processors; geomagnetism detectors including magnetic sensors and magnetometers; reflection of transmitted energy detectors including infrared laser radar sensors, ultrasonic sensors, and microwave radar sensors; electromagnetic induction detectors including inductive-loop detectors; and vibration detectors including triboelectric, seismic, and inertia-switch sensors.

16. The MRI system of claim 14, wherein said at least one parameter p includes one or more of an angle of the image of the $CI_n$ sequence with respect to the first portion of the body part, spatial coordinates of the area of the image of the $CI_n$ sequence, and location of MRI components.

17. The MRI system of claim 14, wherein said detected movement M is characterized by the extent of said movement.

18. The MRI system of claim 14, wherein the processor further performs a Fourier transformation on said $CI_n$ sequence to momentum space (K-space) prior to said analysis.

19. The MRI system of claim 14, wherein said analysis is performed on said $CI_n$ sequence in K-space.

* * * * *